United States Patent
Inoue et al.

(10) Patent No.: US 8,827,254 B2
(45) Date of Patent: Sep. 9, 2014

(54) SUBSTRATE TRANSFER PROCESSING APPARATUS

(75) Inventors: Yuya Inoue, Chigasaki (JP); Tamotsu Tanifuji, Chigasaki (JP); Hisato Tanaka, Chigasaki (JP); Makoto Takahashi, Hidaka (JP); Kuniyoshi Sekine, Hidaka (JP)

(73) Assignee: Ulvac, Inc., Chigasaki-shi (JP)

( * ) Notice: Subject to any disclaimer, the term of this patent is extended or adjusted under 35 U.S.C. 154(b) by 1036 days.

(21) Appl. No.: 12/877,319

(22) Filed: Sep. 8, 2010

(65) Prior Publication Data

US 2011/0048319 A1 Mar. 3, 2011

Related U.S. Application Data

(63) Continuation of application No. PCT/JP2009/054857, filed on Mar. 13, 2009.

(30) Foreign Application Priority Data

Mar. 19, 2008 (JP) ................................. 2008-071479

(51) Int. Cl.
*B23Q 1/25* (2006.01)
*B65G 49/06* (2006.01)
*H01L 21/677* (2006.01)
*G01N 21/956* (2006.01)

(52) U.S. Cl.
CPC .......... *B65G 49/065* (2013.01); *B65G 2249/04* (2013.01); *G01N 21/956* (2013.01); *H01L 21/67742* (2013.01)
USPC ............................... 269/55; 269/75; 29/281.1

(58) Field of Classification Search
USPC .............. 269/55, 60, 289 R, 21, 75; 29/281.1
See application file for complete search history.

(56) References Cited

U.S. PATENT DOCUMENTS

| | | | | |
|---|---|---|---|---|
| 5,116,174 A | * | 5/1992 | Fried et al. ...................... | 409/79 |
| 2006/0291988 A1 | * | 12/2006 | Machiyama et al. ....... | 414/792.7 |
| 2011/0042876 A1 | * | 2/2011 | Inoue et al. ..................... | 269/58 |
| 2011/0048319 A1 | * | 3/2011 | Inoue et al. .................... | 118/300 |

FOREIGN PATENT DOCUMENTS

| | | |
|---|---|---|
| JP | 7-311375 | 11/1995 |
| JP | 9-131632 | 5/1997 |
| JP | 11-317440 | 11/1999 |
| JP | 2002-365026 A1 | 12/2002 |
| JP | 2005-114882 A1 | 4/2005 |
| JP | 2006-224039 A1 | 8/2006 |

OTHER PUBLICATIONS

International Search Report for International Application No. PCT/JP2009/054857 dated Mar. 26, 2009.

* cited by examiner

*Primary Examiner* — Lee D Wilson
(74) *Attorney, Agent, or Firm* — Kratz, Quintos & Hanson, LLP

(57) ABSTRACT

A substrate transfer processing apparatus capable of processing a substrate at high speed is provided. A mounting table on which a substrate is mounted includes a plate-shaped main body and a recessed part formed in a rear surface of the plate-shaped main body. Since the mounting table is lightweight as compared to the mounting table before the recessed part is formed therein, the load on a motor is small and the running cost is low even when the mounting table is moved at high speed. Because the plate-shaped main body is made of granite, the mounting surface can be made flat and smooth by polishing. Since the mounting surface is flat and smooth, the accuracy in positioning the substrate is high.

1 Claim, 3 Drawing Sheets

SUBSTRATE TRANSFER PROCESSING APPARATUS

This application is a continuation of International Application No. PCT/JP2009/054857 filed Mar. 13, 2009, which claims priority to Japanese Patent Document No. 2008-071479, filed on Mar. 19, 2008. The entire disclosures of the prior applications are herein incorporated by reference in their entireties.

BACKGROUND

The present invention relates to processing apparatuses which perform a substrate processing while transferring a substrate.

Conventionally, a substrate transfer apparatus (such as, a moving stage) has been used in performing a substrate processing while moving a processing unit such as a print head, and a substrate relative to each other.

In such a substrate transfer apparatus, the flatness and smoothness of a mounting surface for mounting a substrate is required in order to control a positional relationship between the processing unit and the substrate with high accuracy. Conventionally, the required flatness was around 100 µm, while in recent years a higher flatness (50 µm or less) has been required.

A method is known wherein a material (such as, granite) having a high hardness, is polished to form a substrate-mounting table.

However, granite is heavy in weight, and in order to move the substrate-mounting table at a high speed, a high-power moving unit and a control unit are required, thereby resulting in an increase in equipment cost and running cost (driving power or the like). Moreover, with an increase in the size of the substrate in recent years, the size of the mounting table has also increased; and thus, a reduction in the weight of the mounting table has been further required.

If the thickness of the mounting table made of granite is reduced, the strength of the mounting table decreases although the weight thereof can be reduced. Moreover, if the mounting table is thinned, the mounting table will bend when the mounting table is supported by a support shaft which is disposed upright on an air bearing (or wheel).

In order to improve the flatness of the mounting surface, prior to attaching the mounting table to the support shaft, the mounting table is usually disposed in a processing table, which is wider than the mounting table so as to polish the mounting surface. However, even if the flatness of the mounting surface is set 50 µm or smaller by polishing, and when the mounting table bends due to its attachment to the support shaft, the flatness of the mounting surface will exceed 50 µm.

Such problems are disclosed in, for example, JPA No. 07-311375 and JPA No. 2005-114882.

SUMMARY OF THE INVENTION

The present invention has been made to solve the above-described problems. An object of the present invention is to provide a light-weight mounting table having high surface flatness.

In order to solve the above-described problems, according to an aspect of the present invention, a substrate transfer processing apparatus comprises a track for a substrate, a travel device for a substrate which moves along the track for a substrate and a mounting table which is attached to the travel device for a substrate and a substrate is disposed on a surface of the mounting table. The mounting table includes a plate-shaped main body made of granite and at least one recessed part which is formed by excavating a rear surface of the plate-shaped main body, and the mounting table is supported outside the recessed part, and the substrate is disposed on a surface of the plate-shaped main body opposite to a surface in which the recessed part is formed.

According to another aspect of the present invention, a substrate transfer processing apparatus further comprises a track for processing, a travel device for processing which moves along the track for processing and a processing unit attached to the travel device for processing, each of the track for a substrate and the track for processing being linear-shaped. A direction in which the track for a substrate extends and a direction in which the track for processing extends are perpendicular to each other; and an area where the substrate moves and an area where the processing unit moves overlap with each other.

According to yet another aspect of the present invention, there is provided a substrate transfer processing apparatus, wherein the processing unit includes a print head, and wherein the print head includes a discharge orifice which discharges a processing liquid toward the substrate disposed on the mounting table.

According to yet another aspect of the present invention, there is provided a substrate transfer processing apparatus such that the processing unit is an inspection unit for inspecting the substrate disposed on the mounting table.

The substrate transfer processing apparatus of the present invention is configured as described above, and the mounting table is lightweight as compared to a mounting table of which the recessed part is not formed because of the weight of the formed recessed part; and the equipment cost and running cost of a moving device for moving the mounting table are low.

Because a protruding part (rib) remains around the recessed part, the strength of the mounting table is higher than a case where the board thickness of the mounting table is simply reduced.

If the recessed part is formed in the mounting table, the mounting table is likely to bend when the mounting table is supported by a supporting member, as compared to a case where the recessed part is not formed. If the mounting table is left in the same state such that the mounting table is supported by the supporting member, and the surface of the mounting table on which a substrate is disposed is polished so as to be flat. Then, the surface of the mounting table is flat when the mounting table is actually supported by the supporting member.

Since the mounting table is lightweight, the mounting table can be easily handled and the facility cost and running cost of the moving device for moving the mounting table are also low. The strength of the mounting table is high as compared to a case where the thickness is simply reduced. Since the mounting table is made of granite, a flat and smooth mounting surface can be formed by polishing. Since the mounting surface is flat, the positional relationship between a substrate and the processing unit can be controlled with high accuracy and a desired position of the substrate can be processed accurately.

DETAILED DESCRIPTION OF THE INVENTION

Figure 1:
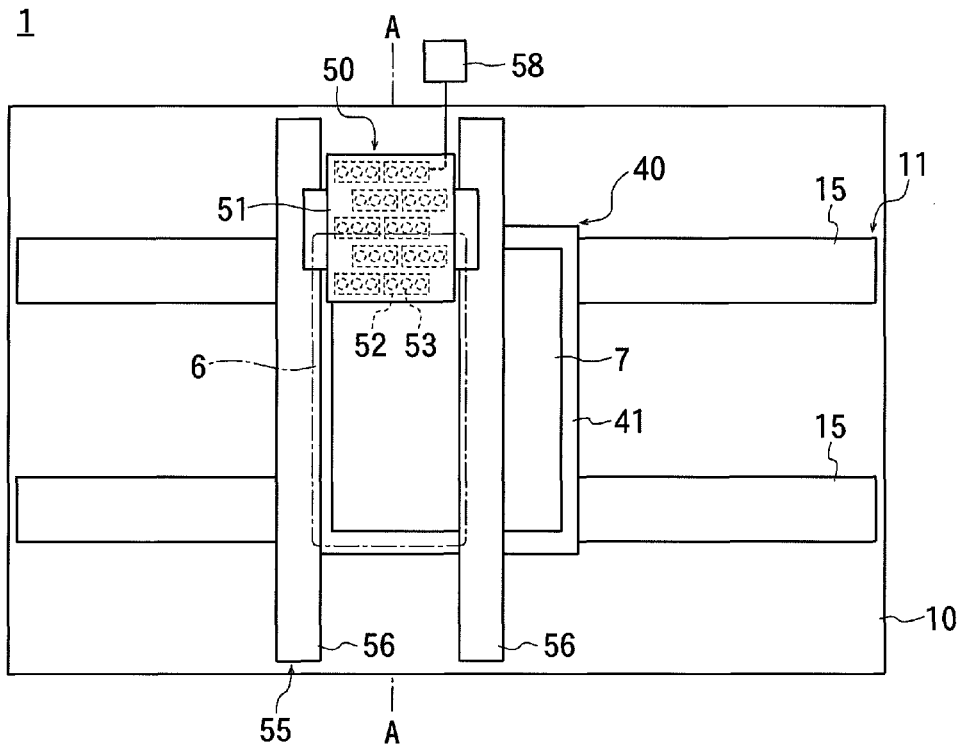
FIG. 1 is a plan view illustrating an example of a substrate transfer processing apparatus of the present invention.
Figure 2:
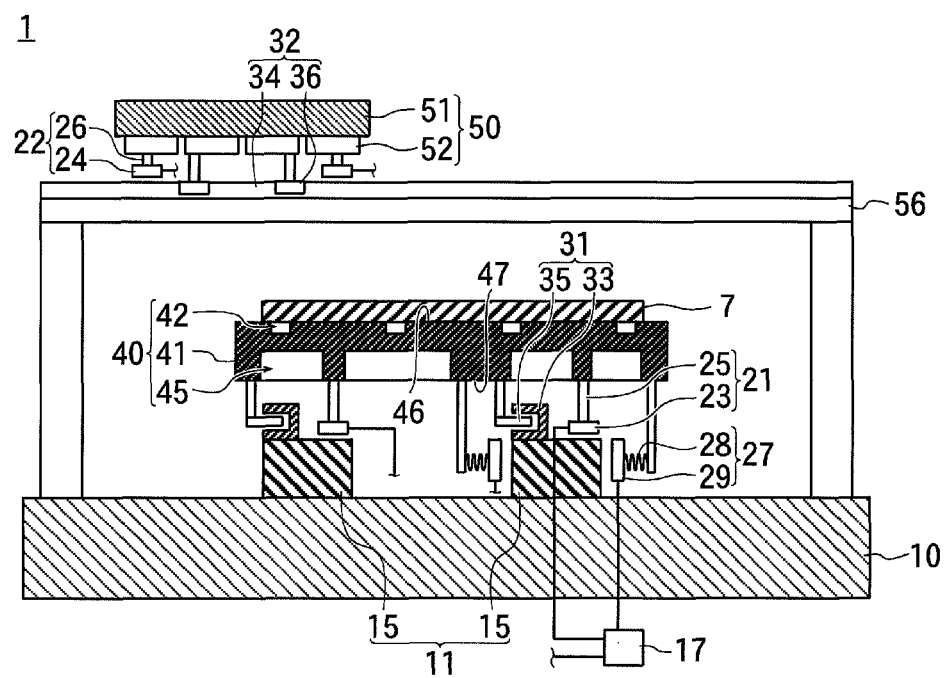
FIG. 2 is a cross-sectional view illustrating the example of the substrate transfer processing apparatus of the present invention.

FIG. 1 is a plan view of a substrate transfer processing apparatus 1 which is an example of a processing apparatus of the present invention; and FIG. 2 is a cross-sectional view along line A-A of FIG. 1.

The substrate transfer processing apparatus 1 includes a pedestal 10, a track 11 for a substrate disposed on the pedestal 10, a travel device 21 for a substrate disposed on the track 11 for a substrate, and a mounting table 40 attached to the travel device 21 for a substrate.

Each track 11 for a substrate includes at least one rail 15.

The rail 15 of the track 11 for a substrate linearly extends on the surface of the pedestal 10. If the number of rails 15 of the track 11 for a substrate is two or more, the extension directions of the respective rails 15 are parallel to each other.

The travel device 21 for a substrate includes an air bearing 23 disposed on the rail 15 and a support shaft (support member) 25 having a lower end which is attached to the air bearing 23.

The number of air bearings 23 is three or more, and one or more air bearings 23 are disposed in each rail 15.

Accordingly, the number of support shafts 25 is also at least three, and at least one support shaft 25 is disposed above the rail 15.

The mounting table 40 is attached in contact with the upper ends of three or more support shafts 25, and is supported above the rail 15 by the support shaft 25.

The air bearing 23 is connected to a gas supply system 17 (such as, an air compressor); and the gas of the gas supply system 17 is supplied to the air bearing 23.

An ejection hole (not shown) is provided in the surface of the air bearing 23 on the rail 15 side; and the gas supplied to the air bearing 23 is ejected from the ejection hole toward the surface of the rail 15 so that the air bearing 23 floats from the rail 15 and the mounting table 40 floats while being supported by the support shaft 25.

The surface of the rail 15 on which the air bearing 23 is disposed is horizontal. The gas supply amount of the gas supply system 17 is set so that each of the lower ends of the respective air bearings 23 floats by the same distance from the surface of the rail 15.

The height from the lower end of each air bearing 23 to the upper end of the support shaft 25 is set to be identical; and accordingly, the upper end of the support shaft 25 (i.e., a portion where the support shaft 25 is in contact with the mounting table 40) is located within a horizontal plane parallel to the surface of the rail 15.

The mounting table 40 includes a plate-shaped main body 41 and a recessed part 45 formed in one surface (rear surface 47) of the plate-shaped main body 41, with a front surface (mounting surface 46) directed upward and the rear surface 47 directed downward; and the upper end of the support shaft 25 is attached in contact with the outer portion (the protruding part around the recessed part: rib) of the recessed part 45 in the rear surface 47.

Even if the mounting table 40 bends when the mounting table 40 is supported by the support shaft 25, the mounting surface 46 becomes flat as discussed later. Here, the mounting surface 46 is horizontal and the substrate 7 is horizontally disposed in close contact with the mounting surface 46.

A groove 42 is formed in an area of the mounting surface 46 where the substrate 7 is disposed; and the substrate 7 is in close contact with an outer portion of the groove 42 of the mounting surface 46 so that the opening of the groove 42 is covered with the substrate 7. The internal space of the groove 42 is connected to an exhaust system (not shown); and if the interior of the groove 42 is evacuated by the exhaust system, the substrate 7 is sucked to the mounting surface 46 due to a pressure difference.

The travel device 21 for a substrate travels by a moving device 31 while the mounting table 40 is horizontally supported. The moving device 31 includes a stationary magnet unit 33 and a movable magnet unit 35, for example. The stationary magnet unit 33 includes a plurality of magnets disposed along the extension direction of the rail 15; and magnetic poles with different polarities are formed on the surfaces of adjacent magnets to each other.

The movable magnet unit 35 (motor coil) is attached to the mounting table 40. The movable magnet unit 35 faces a part of the stationary magnet unit 33. If an AC voltage is applied to the movable magnet unit 35 in a state such that the mounting table 40 is floated, the mounting table 40 moves along the extension direction of the track 11 for a substrate above the track 11 for a substrate.

The surface of the air bearing 23 is horizontal. The gas supply amount from the gas supply system 17 is set such that the distance between the air bearing 23 and the surface of the rail 15 always becomes constant. Accordingly, the mounting table 40 moves within the horizontal plane; and the substrate 7 also moves within the horizontal plane. If the application of an AC voltage to the movable magnet unit 35 is stopped, the mounting table 40 stops.

A track for processing 55 is disposed at a position above the mounting table 40. The track for processing 55 includes at least one rail 56; and the extension direction of each rail 56 is perpendicular to the extension direction of the rail 15 of the track 11 for a substrate.

A travel device for processing 22 is disposed on the track for processing 55, and a processing unit 50 (here, a print head) is attached to the travel device for processing 22. The travel device for processing 22 travels on the rail 56 by a moving device 32; and the processing unit 50 moves along the extension direction of the rail 56. Accordingly, the moving direction of the mounting table 40 is perpendicular to the moving direction of the processing unit 50.

The track 11 for a substrate crosses the track for processing 55 under the track for processing 55 and both ends of the track 11 in the extension direction protrude from an area where the processing unit 50 moves.

Reference numeral 6 of FIG. 1 denotes a processing area which is a part of an area where the processing apparatus 50 moves, and located right above the track 11 for the substrate.

Among two portions protruding from the processed area 6 of the track 11 for a substrate, one portion is defined as a start position and the other one is defined as a turn-back position, wherein the mounting table 40 moves back and forth between the start position and the turn-back position.

A substrate lifting mechanism (not shown) is disposed at the start position. For example, the substrate lifting mechanism includes a lifting pin (not shown); and the mounting table 40 has through-holes (not shown) into which the lifting pin can be inserted. The lifting pins move vertically inside the through-holes of the mounting table 40 which stands still at the start position; and the substrate 7 is placed on the upper end of the lifting pin and is detached from the mounting table 40.

The substrate 7 is placed on the mounting surface 46 at the start position, and the mounting table 40 moves back and forth under the processed area 6; and then, the substrate 7 is removed after its return to the start position. Accordingly, an area where the substrate 7 travels overlaps with an area where the processing unit 50 travels; and the substrate 7 crosses the processed area 6 under the processed area 6.

The track for processing 55 crosses the track 11 for a substrate above the track 11 for a substrate; and both ends thereof in the extension direction protrude from the track 11 for a substrate. The processing unit 50 moves back and forth between one of the portions of the track for processing 55 protruding from the track 11 for a substrate and the other portion; and the processing unit 50 faces the substrate 7 which crosses the processed area 6 while moving back and forth.

The processing unit 50 includes a head main body 51 and at least one print head 52. The print head 52 includes at least one discharge orifice 53 and is attached to the head main body 51 with the discharge orifice 53 directed downward.

Each print head 52 is connected to a coating liquid supply system 58; and coating liquid (such as, ink, spacer dispersion liquid, or the like) supplied from the coating liquid supply system 58 is supplied to each print head 52 and is discharged from the discharge orifice 53.

The substrate 7 faces the processing unit 50 under the processed area 6; and the coating liquid lands on the surface of the substrate 7 so as to coat the same. On the surface of the substrate 7, a portion to be processed to which the coating liquid is to be applied is determined in advance.

The length of the portion to be processed along the moving direction of the processing unit 50 is longer than the length of an area where the processing unit 50 can apply the coating liquid at a time.

The substrate 7 is disposed under the travel area of the processing unit 50, and the processing unit 50 is caused to travel so as to cross the travel area above the substrate 7 (forward movement) while discharging coating liquid, then the coating liquid is applied from one end of the portion to be processed in the moving direction of the processing unit 50 to the other end.

If the length of portion to be processed along the moving direction of the substrate 7 is longer than the length of an area where the processing unit 50 can apply the coating liquid at a time, after the processing unit 50 is moved forward, the substrate 7 is moved so as to dispose an unprocessed part in the portion to be processed to which the coating liquid has not been applied at just under the travel area of the processing unit 50.

In such a state, when the processing unit 50 is caused to travel in the backward direction which is an inverse direction to the forward movement and crosses the portion to be processed (return movement) while discharging the coating liquid, the coating liquid is applied to the unprocessed part in the portion to be processed.

When the processing unit 50 crosses the portion to be processed and the movement of the substrate 7 are repeated, the coating liquid can be applied to the whole portion to be processed.

For the processing unit's 50 crossing of the portion to be processed, the processing unit 50 may be caused to travel while discharging the coating liquid, or the discharging of the coating liquid and the traveling of the processing unit 50 may be alternately repeated.

The printing unit is not limited in particular, and other coating unit (such as, a roll coater or a dispenser) can be used as long as it can apply the coating liquid while moving. Furthermore, the processing unit 50 is not limited to the printing unit; and the portion to be processed of the substrate 7 may be inspected (observed) using an inspection unit (such as, a microscope or a camera).

Figure 3:
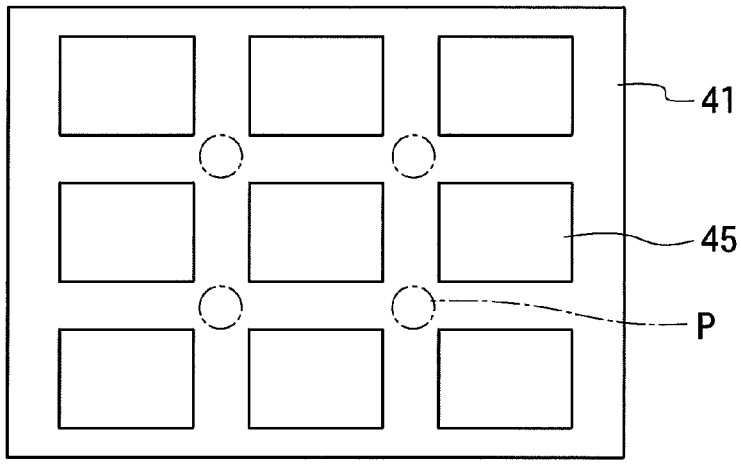
FIG. 3 is a plan view illustrating a first example of a mounting table.
Figure 4:
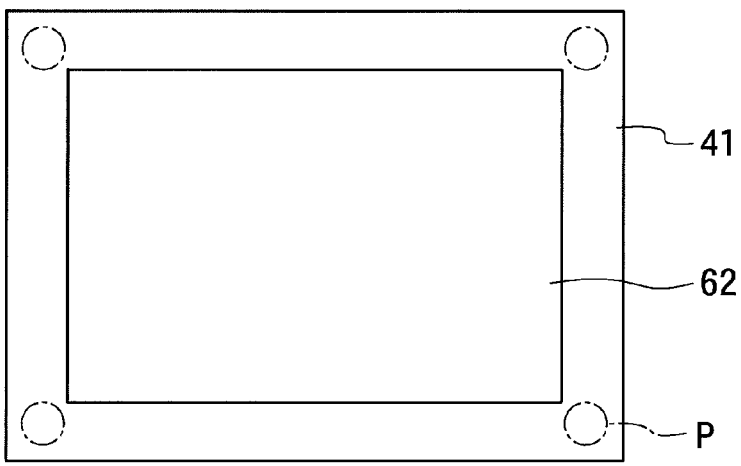
FIG. 4 is a plan view illustrating a second example of the mounting table.
Figure 5:
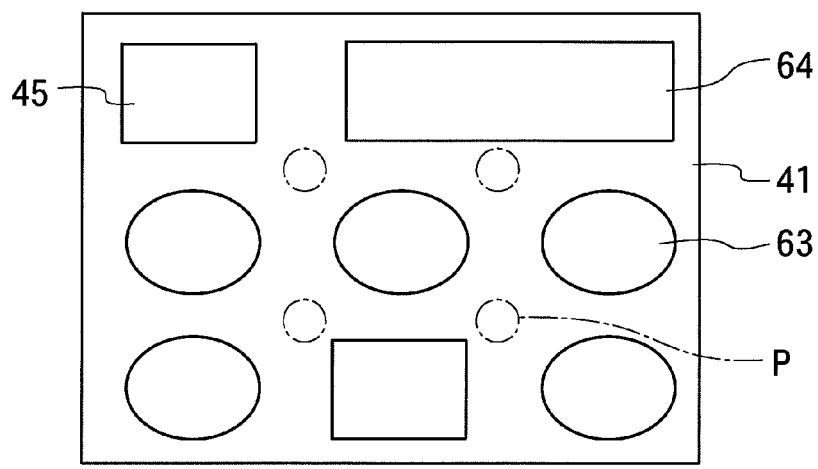
FIG. 5 is a plan view illustrating a third example of the mounting table.

Next, the recessed part 45 of the mounting table 40 and an installation place of the support shaft 25 will be described in detail. FIG. 3 to FIG. 5 are plan views showing the recessed part 45 and an installation place P of the support shaft 25.

As shown in FIG. 3 and FIG. 4, the planar shape of the recessed parts 45, 62 may be rectangular (including square or rectangle), and as shown in FIG. 5, the planar shape of the recessed part 63 may be circular (including true circle or ellipse). Furthermore, the planar shape of the recessed part may be triangular or polygonal.

Moreover, as shown in FIG. 5, the recessed parts 45, 63 having different shapes may be formed in one plate-shaped main body 41, and the recessed parts 45, 64 having different sizes may be formed in one plate-shaped main body 41.

The number of recessed parts 45, 62, and 63 may be plural as shown in FIGS. 3 and 5, or may be one as shown in FIG. 4.

It is preferable that the shape and size of the recessed part are determined in consideration of the center of gravity thereof and balance of the mounting table 40. Specifically, the shape and size of the recessed part are determined so that the load on the support shafts 25 becomes uniform. Alternatively, they are preferably determined such that a rotation moment does not occur at the time of acceleration or deceleration.

The installation place where the support shaft 25 is installed is not limited in particular as long as it is in the rear surface of the plate-shaped main body 41. However, the support shaft 25 is preferably provided in a protruding part on the outer side of the recessed part 45 because the bottom surface of the recessed part 45 is thin and its strength is poor.

As shown in FIGS. 3 and 5, if a place where protruding parts extending between the recessed parts 45 and 63 intersect with each other is set as the installation place P, the strength will increase.

In order to stably hold the mounting table 40, at least three installation places P are necessary, and more preferably, four or more installation places P are required. In order to provide four or more installation places P in places where the protruding parts intersect with each other, nine or more recessed parts 45, 63 are required.

Next, a manufacturing process of the mounting table 40 will be described.

FIG. 6(*a*) shows the plate-shaped main body 41 before the recessed part 45 is formed therein. The plate-shaped main body 41 is made of a granite plate.

In one surface (rear surface 47) of the plate-shaped main body 41, the installation place P of the support shaft 25 described above is determined in advance. In the rear surface 47 of the plate-shaped main body 41, a portion excluding the installation place P and the edge part is excavated in order to form the recessed part 45; and the installation place P and edge part are left without being excavated (FIG. 6 (*b*)). It is noted that the depth of each recessed part 45 may be the same or may be different from each other.

The number of support shafts 25 attached to the mounting table 40 is determined in advance. The same number of support shafts for polishing (support member for polishing) 12 as the support shafts 25 are disposed upright so as to locate the upper end thereof within the same flat surface (the same horizontal plane), and the plate-shaped main body 41 is placed on the support shaft for polishing 12 such that each installation place P is in contact with the support shaft for polishing 12 (FIG. 6(c)).

Because the contact area between the support shaft for polishing 12 and the plate-shaped main body 41 is smaller than the rear surface of the plate-shaped main body 41, a portion around the installation place P of the plate-shaped main body 41 drops below the installation place P and the plate-shaped main body 41 bends.

The shape and size of a portion (upper end) of the support shaft for polishing 12 where the support shaft for polishing 12 is in contact with the plate-shaped main body 41 have the same shape and size as that of the support shaft 25 of a portion (upper end) where the support shaft 25 is in contact with the plate-shaped main body 41. Accordingly, the bend when the plate-shaped main body 41 is supported by the support shaft for polishing 12 is the same as that when the plate-shaped main body 41 is supported by the support shaft 25.

Figure 6A:
FIGS. 6(a) to 6(e) are cross-sectional views illustrating the steps of manufacturing the mounting table.
Figure 6B:
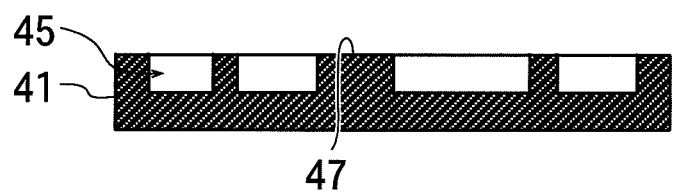
Figure 6C:
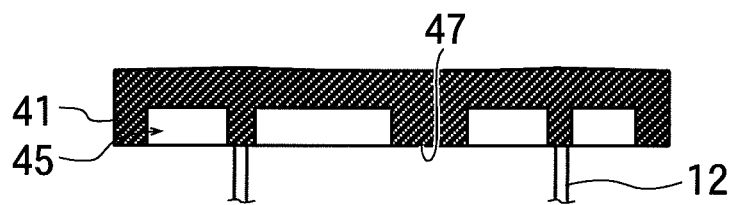
Figure 6D:
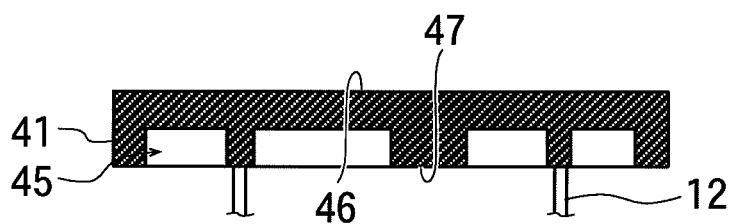

In a state such that when the plate-shaped main body 41 is supported by the support shaft for polishing 12, the mounting surface 46 is polished so as to set the flatness of the mounting surface 46 to be 16 µm or less (the height from a reference plane is in the range of +8 µm to −8 µm) (the lapping process in FIG. 6(d)).

Figure 6E:
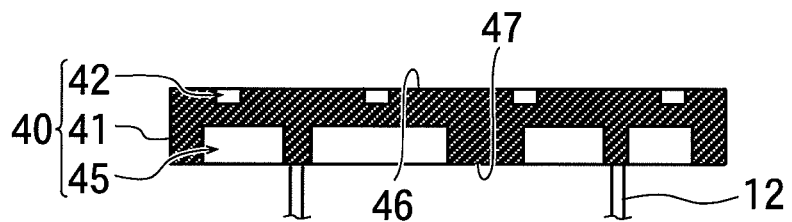

When it is necessary to form the groove 42 and/or a hole for connecting groove 42 to the exhaust system or, the like, the mounting surface 46 is excavated so as to form groove 42 or the hole after the lapping process in a state such that the plate-shaped main body 41 is supported by the support shafts for polishing 12 (FIG. 6(e)).

The flatness of the surface of the mounting surface 46 is measured after the formation of the groove 42 or the hole. If needed, the mounting surface 46 is polished so as to set the flatness to be 16 µm or less (finish lapping process) in a state such that the plate-shaped main body 41 is supported by the support shaft for polishing 12. It is noted that, if the groove 42 or the hole is formed in the mounting surface 46, the flatness of a portion where the mounting surface 46 is in contact with the substrate 7 (i.e., the flatness of a portion of an outer part of the groove 42 or hole) is set to be 16 µm or less.

The support shaft for polishing 12 is removed from the installation place P of the mounting table 40 which has been manufactured in the above-discussed processes; and the upper end of each support shaft 25 is in contact with the installation place P, thereby the mounting table 40 being attached to the support shaft 25.

As discussed above, the shape and size of a portion where the support shaft for polishing 12 is in contact with the mounting table 40 are similar to the shape and the size of the support shaft 25; and the installation place P where the support shaft for polishing 12 is attached to the mounting table 40 is also similar to the installation place P of the support shaft 25. Accordingly, when the mounting table 40 is supported by the support shaft 25, the mounting surface 46 has a flat surface having the flatness of 16 µm or less.

The grinding method in the lapping process and finish lapping process is not limited in particular. One example of such grinding method is a wet lapping method in which the polishing tool and the mounting surface 46 are rubbed with each other in a state such that a polishing liquid formed by dispersing abrasive grains into a solution (water, an organic solvent or the like) is interposed between a polishing tool (lapping tool) and the mounting surface 46.

The abrasive grain is also not limited in particular, and a fine powder of diamond, silicon carbide, alumina, or the like, or a hydrophilic oxide-based abrasive grain (such as, silicon oxide, cerium oxide, zirconia, or chromium oxide) can be used.

The plate-shaped main body 41 used in the present invention is made of granite.

Metal has a high coefficient of thermal expansion and is likely to deform. If the plate-shaped main body 41 is made of a metal, even if the surface is polished to be flatten and smoothened, a deformation or a residual stress that has occurred during polishing causes a swell on the surface, and it cannot be eliminated. Moreover, ceramic is not suitable for the present invention because the surface thereof is difficult to be made flat and smooth by polishing.

Stone (mineral) (such as, granite) is most suitable for the material of the plate-shaped main body 41 of the present invention because it has a coefficient of thermal expansion lower than metal and can be polished easier than ceramic.

The material of the plate-shaped main body 41 is not limited in particular as long as it is a hard stone which does not cause a crack or the like by being excavated; and granite, marble, or the like can be used. However, granite is most suitable in terms ease in polishing.

If the plate-shaped main body 41 is made of granite, even when the recessed part 45 is excavated and also polished, the plate-shaped main body 41 will not be damaged; and further, the mounting surface 46 which is flatter and smoother than the one made of other materials can be obtained by the polishing.

The type of granite is not limited in particular, and various types (such as, China black, Indian black, Rustenburg, or Kurnool) can be used.

If a part of the plate-shaped main body 41 is made of a different material, the strength significantly decreases, and deformation is likely to occur due to a difference in the coefficients of thermal expansion. Therefore, in the plate-shaped main body 41, all the parts from the mounting surface 46 to the rear surface 47 are preferably made of granite.

The substrate 7 can be held on the mouthing table 40 being pushed to the mounting surface 46 by a pressing member, instead of sucking.

The intersecting angle between the extension direction of the track 11 for a substrate and the extension direction of the track for processing 55 may not be the right angle as long as these extension directions intersect with each other.

The travel device for processing 22 attached to the processing unit 50 is not limited in particular. For example, similar to the travel device 21 for a substrate, the travel device for processing 22 includes the air bearing 24 disposed on the rail 56 and the support shaft (support member) 26 having its lower end attached to the air bearing 24, the upper end of the support shaft 26 being attached to the processing unit 50.

Moreover, the moving device 32 of the processing unit 50 is also not limited in particular; and for example, a stationary magnet unit 34 and movable magnet unit 36 similar to those of the moving device 31 of the mounting table 40 may be attached to the rail 56 and the processing unit 50, respectively, so as to constitute the moving device 32.

As discussed above, a case has been described where the mounting table 40 and the processing unit 50 are attached to the upper ends of the support shafts 25, 26 so as to travel on the rails 15, 56, respectively. However, the present invention is not limited thereto.

For example, the sides of the support shafts 25, 26 and opposite side to the air bearings 23, 24 (or wheels) may be folded downward and upward, respectively; and on their folded ends, the mounting table 40 and the processing unit 50 may be placed so that the mounting table 40 and the processing unit 50 are disposed below the rails 15, 56.

Also in this case, a full weight load of the mounting table 40 is applied to the support shaft 25; and therefore, when the mounting table 40 is manufactured, the support shaft for polishing 12 is attached to the installation place P, to which the support shaft 25 is to be attached, and polishing is performed in such a state that the mounting table 40 is supported by the support shaft for polishing 12.

The configurations of the travel device 21 for a substrate and the travel device for processing 22 are also not limited in particular; and instead of the air bearings 23 and 24, a wheel may be attached to the support shafts 25 and 26, respectively. If the wheel is used instead of the air bearings 23 and 24, the moving devices 31 and 32 are set as motors for rotating this wheel.

As discussed above, a case has been described such that each of the substrate 7 and the processing unit 50 is moved. However, the present invention is not limited thereto. For example, a rail is extended on the surface of the pedestal 10, and the track 11 for a substrate is disposed so as to be perpendicular to this rail. If the track 11 for a substrate is moved along a rail perpendicular to the extension direction of the track 11, then the substrate 7 will move in two directions (i.e., the direction along the track 11 for a substrate and the direction perpendicular to the track 11 for a substrate); and therefore, it is not necessary to move the processing unit 50.

In order to prevent the occurrence of the derailment from the track 11 for a substrate, a derailment-preventing device 27 as shown in FIG. 2 may be attached to the mounting table 40. The derailment-preventing device 27 includes two or more air bearings 29 attached to the mounting table 40, for example. Since the air bearing 29 is located on both sides of the rail 15 and is pushed against the rail 15 by a spring member 28 from both sides, the mounting table 40 does not derail from the rail 15.

The invention claimed is:

1. A substrate transfer processing apparatus, comprising:
a track for a substrate;
a travel device for a substrate which moves along the track for a substrate;
a track for processing;
a travel device for processing which moves along the track for processing;
a processing unit attached to the travel device for processing; and
a mounting table which is attached to the travel device for a substrate and has a substrate disposed on a surface of the mounting table, the mounting table including a plate-shaped main body made of granite and at least one recessed part which is formed by excavating a rear surface of the plate-shaped main body,
wherein the mounting table is supported outside the recessed part,
wherein the substrate is disposed on a surface of the plate-shaped main body opposite to a surface in which the recessed part is formed,
wherein each of the track for a substrate and the track for processing is linear-shaped,
wherein a direction in which the track for a substrate extends and a direction in which the track for processing extends are perpendicular to each other,
wherein an area where the substrate moves an area where the processing unit moves overlap with each other,
wherein the processing unit includes a print head, and
wherein the print head includes a discharge orifice which discharges a processing liquid toward the substrate disposed on the mounting table.

* * * * *